United States Patent
Kong

[19]

[11] Patent Number: 6,053,888
[45] Date of Patent: Apr. 25, 2000

[54] VARIABLE VOLUME BOTTLE AND RELATED MEDICAL FLUID INFUSION SYSTEM

[76] Inventor: Carl Cheung Tung Kong, 6122 Whittier Blvd., Los Angeles, Calif. 90022

[21] Appl. No.: 09/129,715

[22] Filed: Aug. 5, 1998

[51] Int. Cl.⁷ .................................................. A61M 31/00
[52] U.S. Cl. ............................................ 604/67; 604/131
[58] Field of Search .................................. 604/150, 131, 604/67

[56] References Cited

U.S. PATENT DOCUMENTS

| | | |
|---|---|---|
| Re. 32,065 | 1/1986 | Ralston, Jr. et al. . |
| 1,973,262 | 9/1934 | McQueen, Jr. ............ 604/150 |
| 3,589,422 | 6/1971 | Bellamy, Jr. . |
| 3,777,697 | 12/1973 | Woessner . |
| 3,895,741 | 7/1975 | Nugent . |
| 4,010,783 | 3/1977 | Ralston . |
| 4,029,094 | 6/1977 | Winicki . |
| 4,049,033 | 9/1977 | Ralston, Jr. . |
| 4,088,166 | 5/1978 | Miller . |
| 4,090,514 | 5/1978 | Hinck et al. . |
| 4,090,541 | 5/1978 | Cammarata, III et al. . |
| 4,096,897 | 6/1978 | Cammarata, III . |
| 4,160,473 | 7/1979 | Winchell . |
| 4,191,231 | 3/1980 | Winchell et al. . |
| 4,308,904 | 1/1982 | Martin et al. . |
| 4,553,970 | 11/1985 | Lewis, Jr. . |
| 4,857,042 | 8/1989 | Schneider . |
| 5,006,118 | 4/1991 | Yule . |
| 5,074,839 | 12/1991 | Choksi et al. . |

*Primary Examiner*—Jeffrey A. Smith
*Attorney, Agent, or Firm*—Kelly Bauersfeld Lowry & Kelley, LLP

[57] ABSTRACT

A variable volume bottle and related system are provided for infusing a selected medical fluid to a patient. The variable volume bottle comprises a relatively rigid bottle body having a lower neck adapted for connection to an infusion line by a cap fitting having a slotted nipple for controlled flow of the medical fluid from the bottle and through the infusion line to the patient. The bottle body further includes a movable upper wall which descends as the fluid is delivered to the patient, and a flow sensor unit tracks displacement of the movable upper wall to provide an indication of the dispensed fluid volume. A flow rate controller may be provided for constricting the slotted nipple to variably adjust the open area defined by the slot therein, and thereby variably select the rate of fluid flow to the patient. In an alternative embodiment, the cap fitting may comprise a pair of interfitting cap members having a pair of overlapping flow ports formed therein, wherein the cap members are movably positioned with respect to each other to adjust the open area of an outlet passage defined by the flow ports and thereby variably select the rate of fluid flow to the patient.

25 Claims, 7 Drawing Sheets

VARIABLE VOLUME BOTTLE AND RELATED MEDICAL FLUID INFUSION SYSTEM

BACKGROUND OF THE INVENTION

This invention relates generally to devices and systems for administering medical fluids to a patient by intravenous infusion or the like. More particularly, this invention relates to an improved variable volume bottle for containing a medical fluid, wherein the bottle includes improved means for monitoring the fluid volume dispensed to the patient, and further includes improved and relatively simplified means for variably adjusting the rate of fluid flow to the patient.

Fluid containers such as bottles and plastic bags are well known in the art for use in the administration of a selected medical fluid such as a saline solution or the like to a patient, such as by intravenous infusion. Such fluid containers are typically mounted at an elevated position relative to the patient and include a lower neck or the like adapted for connection to a length of flexible infusion tubing which is coupled in turn to the patient by means of a catheter or the like. The medical fluid within the container is allowed to flow by gravity, in the case of intravenous infusion, through the infusion tubing to the patient. A flow rate regulation means such as a roll clamp mounted along the infusion tubing is normally provided to variably select the rate of fluid flow to the patient. In addition, the fluid container is commonly formed from a transparent or partially transparent material and includes a volumetric scale which can be visually compared with the fluid level within the container. With this arrangement, the volume of fluid administered to the patient and, conversely, the volume of fluid remaining within the container, may be determined. However, these fluid volume determinations are only approximations, particularly when the fluid container is a flexible bag which inherently sags and assumes different physical shapes as the fluid is dispensed.

In recent years, devices and systems for delivering medical fluids to patients have become increasingly complex and costly, particularly with respect to variably regulating and monitoring the rate of fluid flow. More specifically, a variety of electronic drop sensors are currently known for detecting and counting individual fluid drops dispensed from the fluid container to the infusion tubing. While such drop sensors provide accurate monitoring of the fluid flow rate and cumulative volume delivered to the patient, they are relatively sophisticated and costly devices which, unfortunately, continue to rely upon manually adjusted setting of a conventional roll clamp in order to increase or decrease the flow rate, as desired. Adjustment of the roll clamp remains a trial and error process, and typically requires considerable skill to adjust quickly to a specific target flow rate.

The present invention relates to an improved medical fluid container and related system for infusing a medical fluid to a patient, including relatively simple and easily adjustable flow rate regulation means in combination with an improved and relatively simplified means for tracking and monitoring the rate and the volume of fluid flow to a patient.

SUMMARY OF THE INVENTION

In accordance with the invention, an improved medical fluid infusion system comprises a variable volume bottle having a substantially rigid and open-ended bottle body defining a neck at one end, and having a base plate movably mounted to an opposite base end of the bottle body. The variable volume bottle is adapted for mounting in an elevated position relative to a patient, in an inverted orientation with the neck opening downwardly for connection to a length of infusion tubing. An adjustable flow rate or pre-set controller is provided for variably selecting the rate of fluid flow from the bottle. The base plate descends within the bottle body as fluid is dispensed, and a flow sensor unit tracks the movement of the base wall to monitor fluid flow rate and dispensed volume.

In a preferred form of the invention, the neck of the variable volume bottle is coupled to the infusion tubing by a cap fitting having a slotted resilient nipple for substantially slow drip flow rate of the medical fluid from the bottle and through the infusion tubing to a patient. The flow rate controller comprises a constriction device for adjusting the open flow area through the resilient nipple, and thereby adjusting the fluid flow rate. The constriction device may comprise a manually or electronically operated clamp. Alternately, the cap fitting may comprise a double cap having interfitting inner and outer cap members with overlapping flow ports formed therein, wherein the cap members are rotatable relative to each other to vary the effective open area of an outlet passage for fluid outflow from the bottle and thereby adjust the fluid flow rate.

The base plate of the variable volume bottle is movably coupled to the base end of the bottle body by a flexible bellows like membrane. The base plate is engaged and followed by a sensor arm of the flow sensor unit, which tracks downward displacement of the base wall into the interior of the bottle body as the fluid is dispensed to the patient. The sensor arm carries at least one conductive contact past a series of conductive pads mounted within a sensor housing, resulting in the generation of a succession of electrical signals coupled to a monitor for monitoring and indicating the dispensed fluid volume.

Other features and advantages of the present invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

Figure 1:
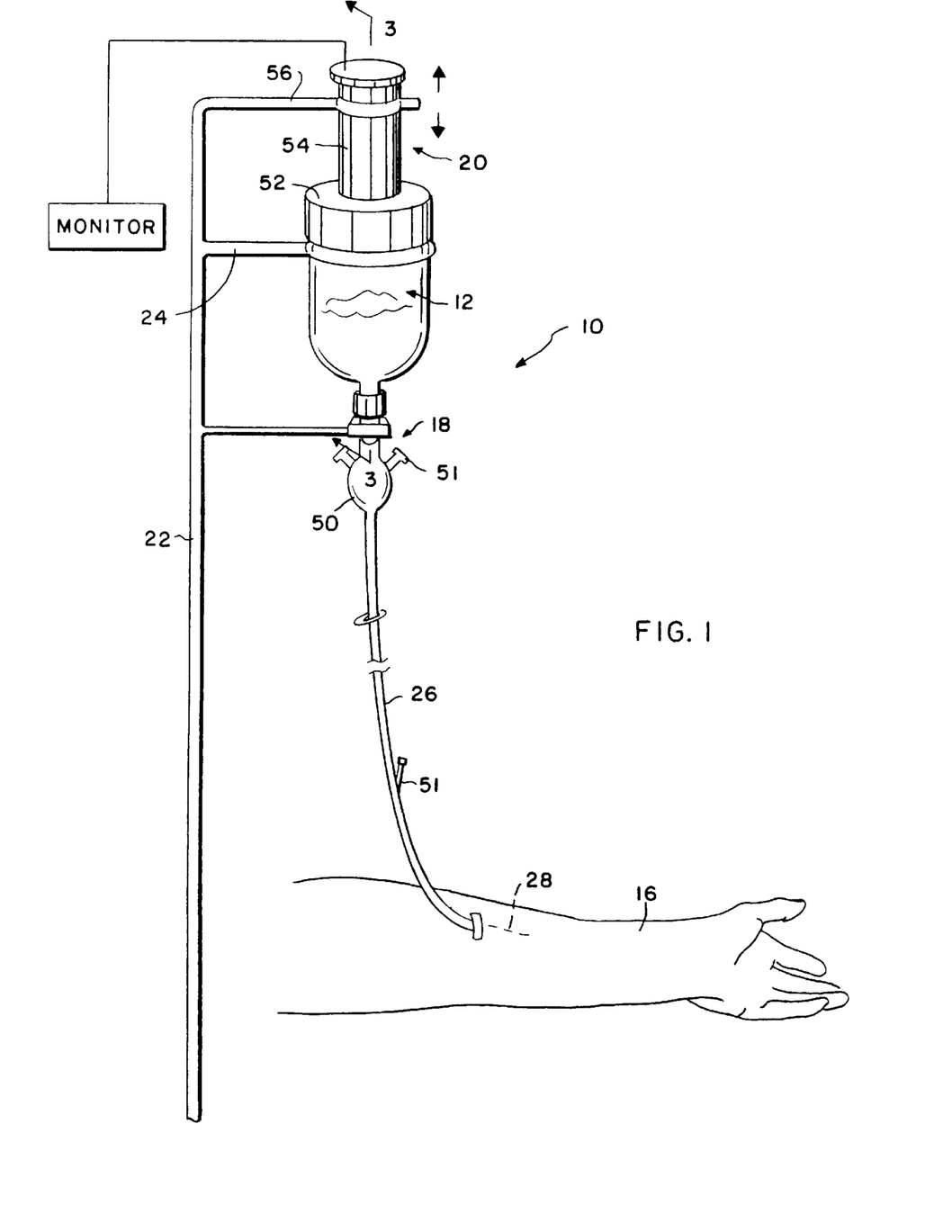
FIG. 1 is a fragmented perspective view illustrating a variable volume bottle and related medication fluid infusion system constructed in accordance with the invention.

As shown in the exemplary drawings, a medication fluid infusion system referred to generally in FIG. 1 by the reference numeral 10 includes a variable volume bottle 12 containing a selected medical fluid 14 (FIG. 2) for administration to a patient 16 by intravenous infusion or the like. The infusion system includes an adjustable flow rate controller 18 for regulating the rate of fluid flow to the patient, and a flow sensor unit 20 for monitoring the fluid flow rate and volume dispensed to the patient.

The fluid infusion system 10 is designed for delivering the selected medical fluid 14 to the patient 16 at a relatively slow and substantially drip flow rate which can be variably set in accordance with the specific medical fluid and patient requirements. Pursuant to conventional fluid infusion systems and methods, the medical fluid 14 is prepackaged for convenient mounting at an elevated position relative to the patient 16, such as by mounting on a standard pole or stand 22 having an appropriate bracket 24 for receiving and supporting the fluid container. The medical fluid 14 drains from the container through a suitable length of infusion tubing 26 for administration to the patient 16 via a catheter 28 or the like, wherein fluid flow to the patient occurs normally by gravity in a low pressure intravenous infusion application. The infusion system 10 of the present invention provides an improved medical fluid container in the form of the variable volume bottle 12 adapted for convenient tracking or monitoring of the dispensed fluid volume over a period of time. In addition, the variable volume bottle 12 is adapted for convenient use in combination with the flow rate controller 18 which has a relatively simplified and easily adjustable construction.

Figure 2:
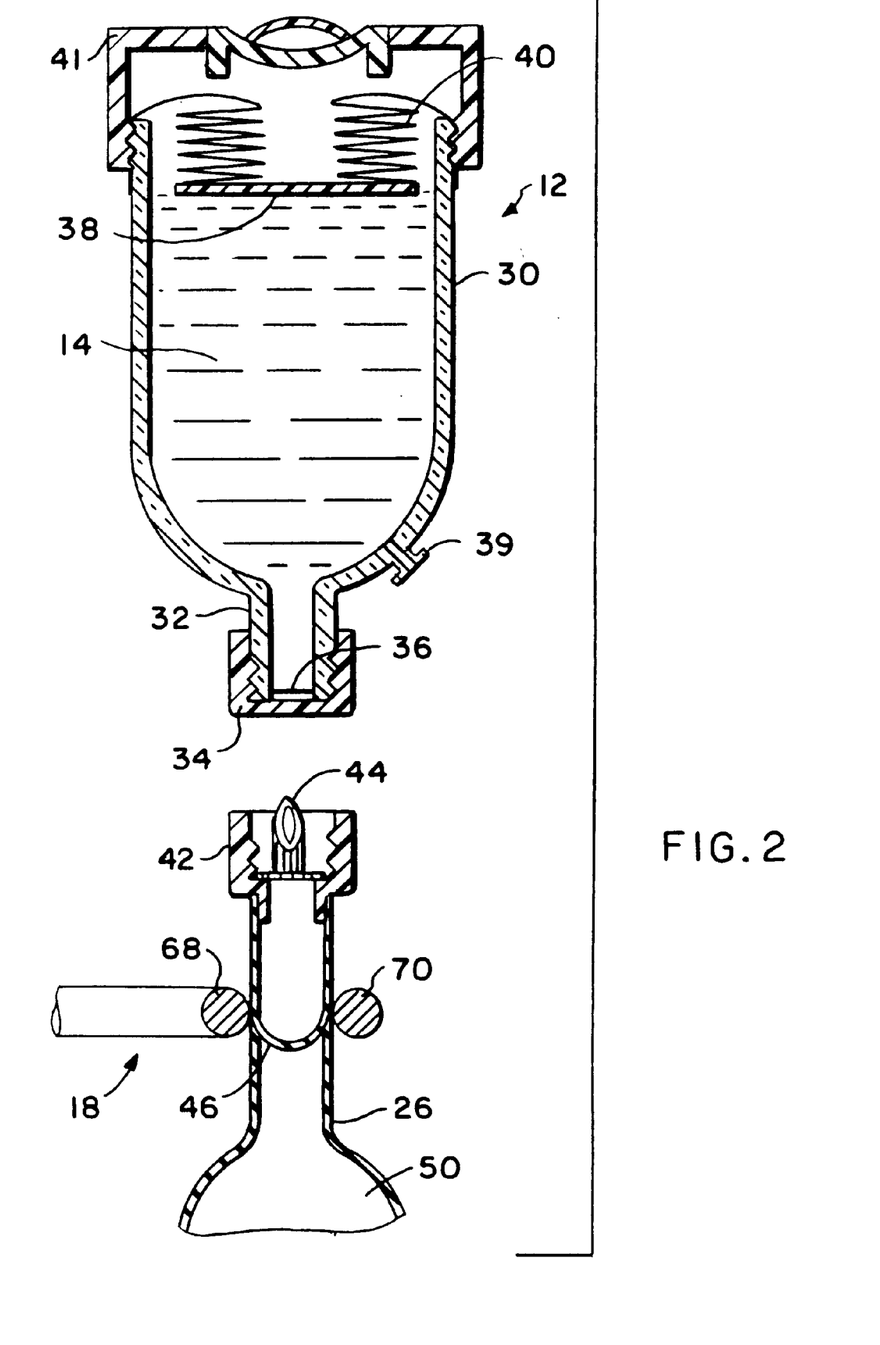
FIG. 2 is an enlarged and exploded vertical sectional view of the variable volume bottle of FIG. 1, depicting assembly thereof with infusion tubing adapted in turn for connection to a patient.
Figure 3:
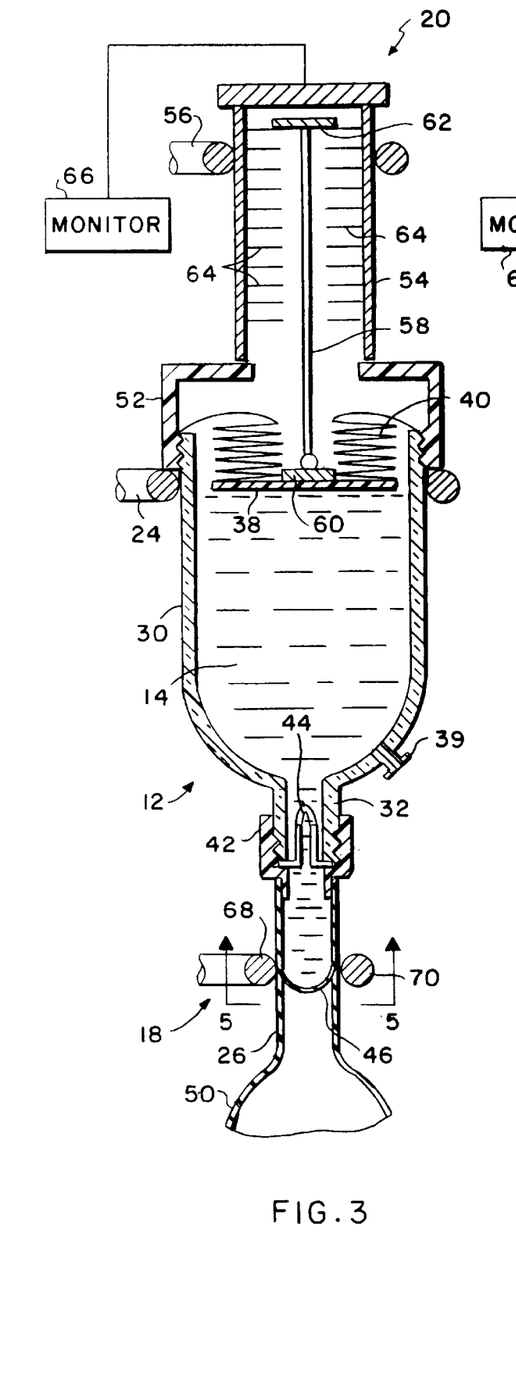
FIG. 3 is an enlarged fragmented vertical sectional view taken generally on the line 3—3 of FIG. 1, and depicting the variable volume bottle in a substantially filled condition.
Figure 4:
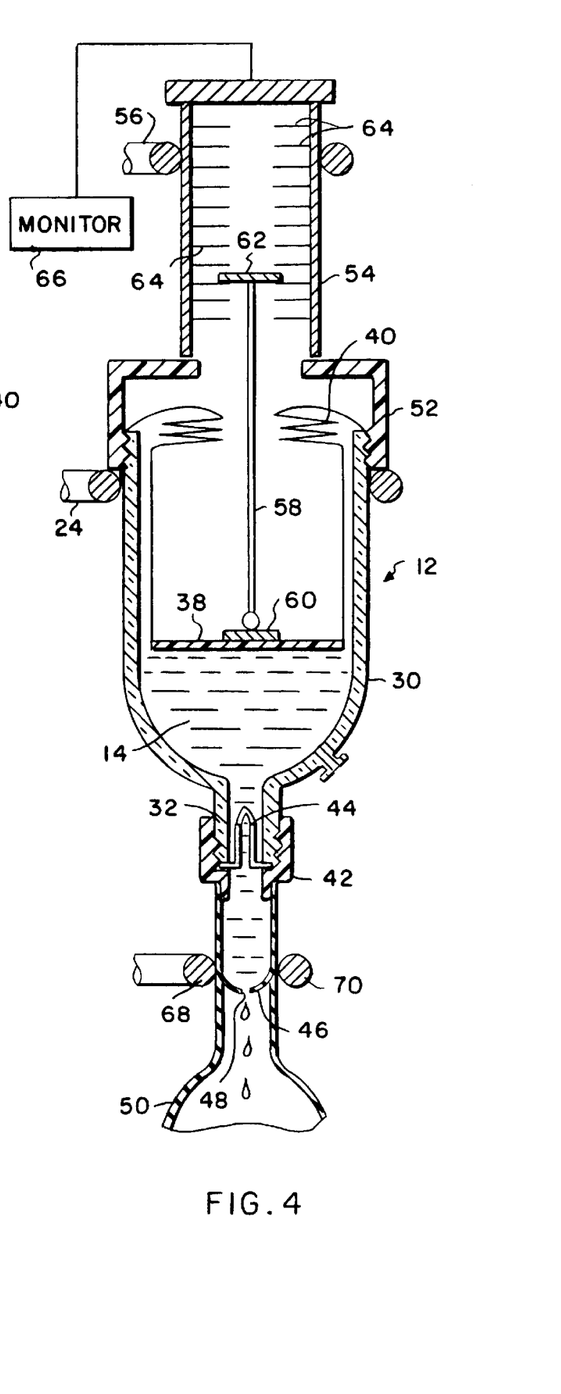
FIG. 4 is a fragmented vertical sectional view similar to FIG. 3, but showing the variable volume bottle in a partially emptied condition.
Figure 5:
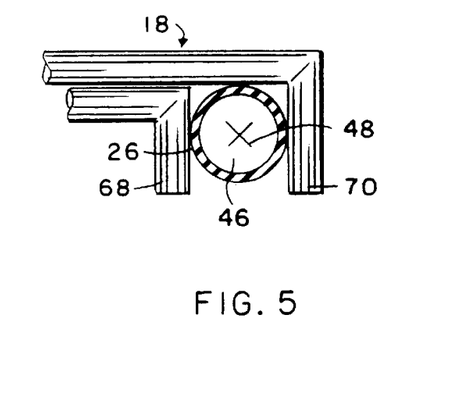
FIG. 5 is an enlarged horizontal sectional view taken generally on the line 5—5 of FIG. 3.
Figure 6:
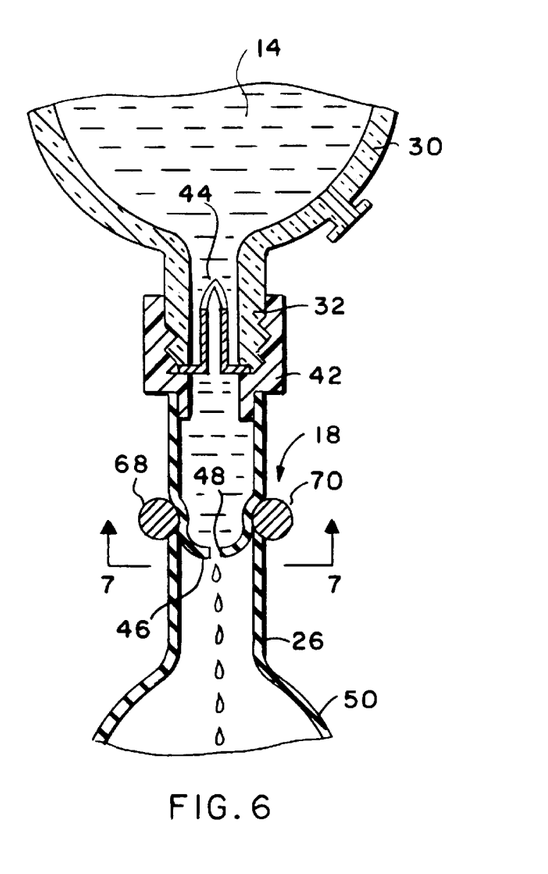
FIG. 6 is a further enlarged and fragmented vertical sectional view similar to a portion of FIG. 3, but illustrating operation of a flow rate controller for variably setting the rate of fluid flow to a patient.
Figure 7:
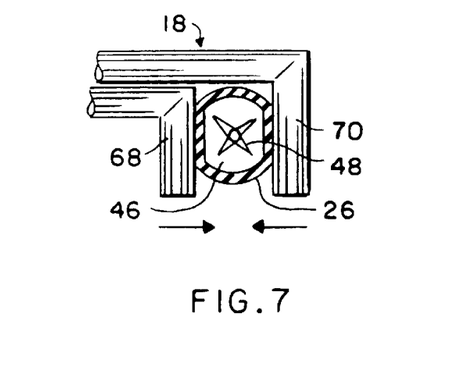
FIG. 7 is a horizontal sectional view taken generally on the line 7—7 of FIG. 6.

As shown in detail in FIGS. 1–4, the variable volume bottle 12 comprises a relatively rigid bottle body 30 formed from glass or a sturdy molded plastic or the like to have a standard open-mouthed neck 32 at one end. The neck 32 is normally closed and sealed by an appropriate cap 34 (FIG. 2) threadably mounted thereon, and in the preferred form the neck 32 additionally includes a piercable membrane or septum 36 mounted beneath the cap 34. Of course, other sealing means could be utilized with or without the cap. The opposite or base end of the bottle body 30 is also open to receive a base plate 38 (FIGS. 2–4) having a generally circular cross sectional shape for slide-fit mounting into the bottle body. The base plate 38 is coupled generally at its periphery to a flexible bellows like annular membrane 40 which is coupled in turn to the bottle body 30 at or near the base end thereof. With this construction, the base plate 38 comprises a movable wall defining a portion of the bottle interior within which the medical fluid 14 is contained. FIGS. 2 and 3 show the base plate 38 is a retracted state disposed substantially at the base end of the bottle body 30, to define a substantially maximum bottle volume substantially filled with the medical fluid. A removable base cap 41 (FIG. 2) may be provided on the base end of the bottle body 30, as by threaded mounting thereon, to provided a rigid exterior container structure suitable for convenient storage and handling prior to use. An injection port 39 may also be provided in the bottle body 30 to permit introduction of a selected medication into the bottle interior.

FIG. 2 illustrates the variable volume bottle 12 having the base cap 41 mounted thereon, with the bottle 12 in an inverted orientation so that the neck 32 is at the lower bottle end. In this orientation, the bottle neck 32 is disposed for quick and easy connection to a cap fitting 42 at the upper or upstream end of the flexible infusion tubing 26. More specifically, upon thread-off removal of the bottle cap 34, the piercable septum 34 retains the medical fluid 14 within the bottle interior while the cap fitting 42 is threadably attached to the neck 32. As shown, the cap fitting 42 comprises a generally annular threaded collar for mounting onto the bottle neck, and additionally carries an upwardly projecting hollow spike 44 for piercing the septum 34 coincident with thread-on attachment of the cap fitting with the bottle neck. Thus, when these components are assembled as described, the medical fluid 14 within the variable volume bottle 12 may flow or drain through the bottle neck 32 and the spike 44 carried by the cap fitting 42 into the upper end of the infusion tubing 26. Connection of the bottle neck 32 with the infusion tubing may take place while the bottle 12 is supported on the stand 22 by the bottle bracket 24, or such connection may be performed substantially immediately prior to placing the bottle 12 on the bottle bracket 24.

In accordance with one aspect of the invention, the upper end of the infusion tubing 26 comprises the relatively simple and variably adjustable flow rate controller 18. In one preferred form as depicted in FIGS. 2–5, the flow rate controller 18 comprises a resilient nipple 46 formed integrally with the infusion tubing and positioned adjacent the cap fitting 42 to define a downwardly open nipple port 48 which may have a generally X-shaped slit configuration as viewed in FIG. 5. This ported resilient nipple 46 comprises a relatively simple drop former allowing downward drain passage of the medical fluid 14 substantially in a succession of individual drops, at a flow rate proportional to the open port flow area. The medical fluid drops falling from the ported nipple 46 pass initially into an enlarged and generally bulb-shaped drip chamber 50 (FIGS. 2–4) which is also formed integrally as a portion of the infusion tubing 26, and may additionally include one or more injection ports 51 (FIG. 1). In this regard, the infusion tubing material is desirably transparent or at least partially transparent to permit visual observation of the medical fluid drops falling from the nipple 46, and also to permit visual observation of the medical fluid within the drip chamber 50. From the bottom of the drip chamber 50, the infusion tubing 26 extends with an appropriate length to the patient 16 for suitable fluid infusion by means of the catheter 28 or the like.

The rate of fluid flow from the inverted bottle 12 to the patient is monitored by the flow sensor unit 20 mounted on the stand 22. More particularly, when the bottle 12 is assembled with the infusion tube 26 as described above, the base cap 41 (FIG. 2) is removed from the bottle to expose the base plate 38 and the associated membrane 40 interconnecting the base plate 38 to the bottle body 30. As the bottle 12 is then mounted on the stand 22, the base end of the bottle body 30 is coupled as by threaded engagement with a lower mounting collar 52 (FIGS. 1, 3 and 4) of the flow sensor unit 20. This mounting collar 52 is located at the lower end of a sensor housing 54 supported from the stand 22 by a suitable sensor bracket 56. Within the sensor housing 54, a sensor track arm 58 is movably carried for vertical displacement in response to fluid dispensing from the bottle 12.

The sensor track arm 58 comprises a vertically oriented element having a lower end coupled to a weighted slug 60 adapted to rest upon an upper outboard face of the base plate 38 of the variable volume bottle 12. As illustrated in FIG. 3, when the bottle 12 is in a substantially filled condition, the sensor arm 58 extends upwardly from the slug 60 to terminate at an upper end positioned within and substantially near the upper end of the sensor unit housing 54. However, as the medical fluid 14 is dispensed from the bottle 12, the sensor arm 58 displaces downwardly with the lower end following the base plate 38 as viewed in FIG. 4, whereby the upper end of the sensor arm also translates downwardly within the sensor housing 54. Importantly, the upper end of the sensor arm 58 carries a conductive contact 62 past a vertically spaced succession of conductive pads 64 on the housing 54, wherein the movement of the contact 62 past the pads 64 resulting in a succession of electrical signals which can be detected by a monitor 66. The monitor 66 may be programmed to translate this movement to a determination of the fluid volume dispensed to the patient, or to determine the remaining fluid volume within the bottle, and to provide a visual display of one or both of these parameters. In addition, the monitor 66 may be programmed to track changes in the monitored fluid volume as a function of time, to provide a visual indication of the rate of fluid flow to the patient. Other sensors may be utilized in place of that described above such as, for example and without limitation, an ultrasonic level transmitter.

Figure 8:
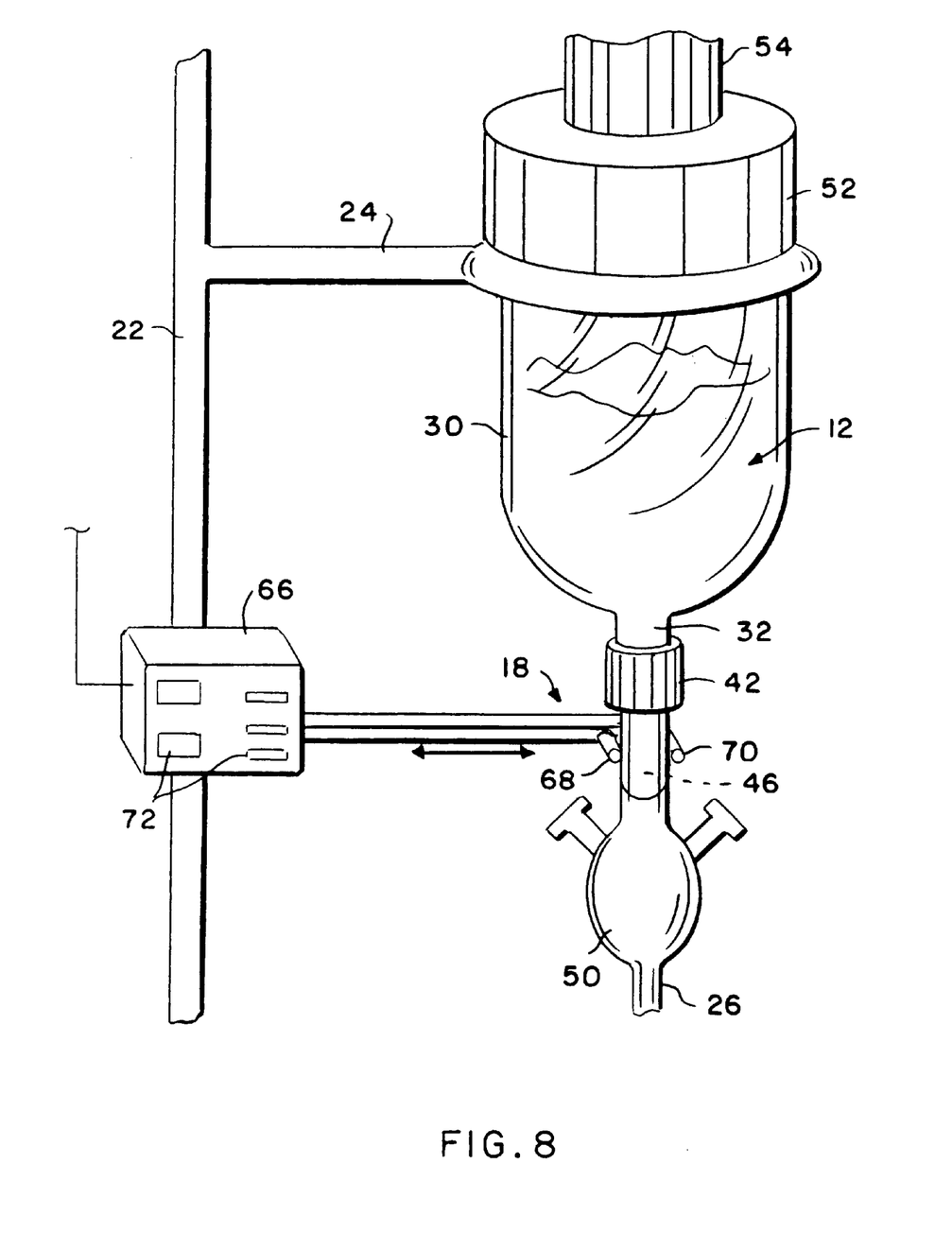
FIG. 8 is a fragmented perspective view showing a further alternative preferred embodiment of the invention.

The monitor 66 thus beneficially provides fluid volume and flow rate information which can be employed to variably adjust the fluid flow rate to a desired setting for the particular medical fluid and patient requirements. In this regard, FIGS. 1–4 and 6–7 illustrate the flow rate controller 18 to include a clamp having movably adjusted jaws 68 and 70 engaging the resilient nipple 46 at a location slightly above the nipple port 48. Appropriate adjustment of the clamp jaws 68, 70 to compress or squeeze the nipple 46 is effective to enlarge the open flow area defined by the nipple port 48, and thereby increase the rate of fluid flow through the nipple, as shown by way of example in FIG. 6 and 7. Such adjustment of the clamp jaws 68, 70 may be performed manually, or alternately the monitor 66 may be coupled directly to the clamp jaws 68, 70 as viewed in FIG. 8 for automated clamp adjustment in response to detected actual flow rate as previously described, and a preset target flow rate inputted to the monitor 66 by appropriate controls 72.

Alternatively, the spacing of the clap jaws 68, 70 may be pre-set to obtain a desired rate of fluid flow. In such a case, a ring having notches of different widths may be utilized to permit selection of one flow rate from several available chores.

Figure 9:
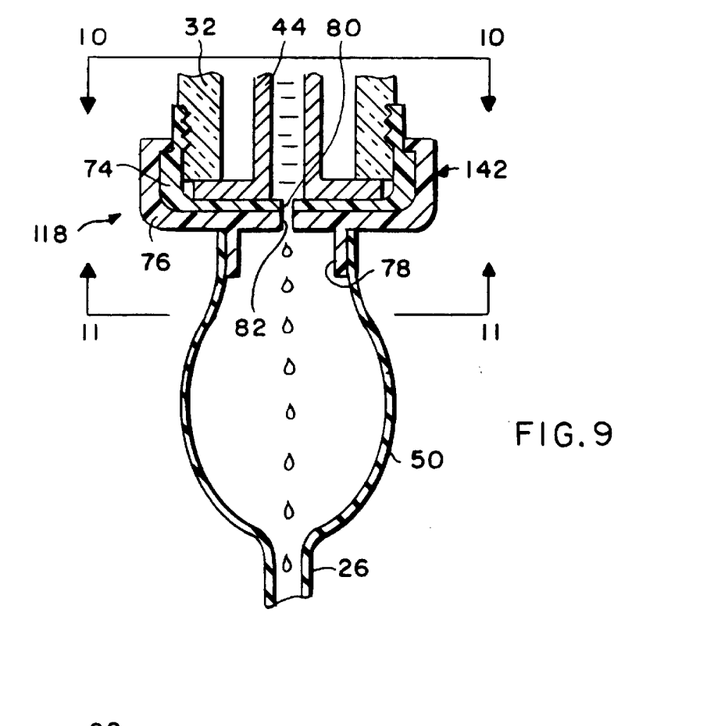
FIG. 9 is an enlarged and fragmented vertical sectional view similar to FIG. 6, and depicting a still further alternative preferred form of the invention including a modified flow rate controller.
Figure 10:
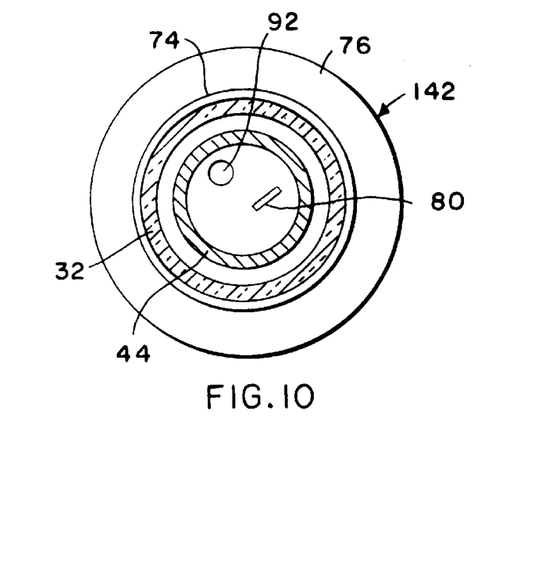
FIG. 10 is a horizontal sectional view taken generally on the line 10—10 of FIG. 9.
Figure 11:
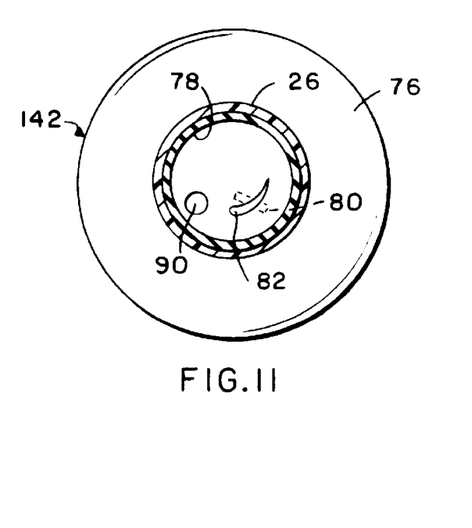
FIG. 11 is a horizontal sectional view taken generally on the line 11—11 of FIG. 9.

FIGS. 9–11 illustrate an alternative flow rate controller 118 for variably regulating the fluid flow rate from the bottle 12, in lieu of the resilient nipple 46 shown and described with respect to FIGS. 1–7. In this embodiment, the modified flow rate controller 118 comprises a portion of a modified cap fitting 142 for mounted onto the neck of the variable volume bottle 12.

More particularly, the modified cap fitting 142 comprises an inner cap 74 adapted for thread-on connection to the bottle neck 32, and for reception as by a snap-fit connection into an outer cap 76. The inner cap 74 supports the hollow spike 44 for piercing the septum 36 which normally closes the mouth of the bottle neck 32. The outer cap 76 is rotatably mounted onto the inner cap 74, and further includes a downwardly extending tubular flange 78 adapted for connection to the upper end of the infusion tubing 26. The inner and outer caps 74, 76 respectively define a pair of flow ports 80 and 82 which overlie each other to cooperatively define an open outlet passage for flow of the medical fluid 14 substantially at a drip flow rate into the drip chamber 50 near the upper end of the infusion tubing. These flow ports 80, 82 are positioned off-axis relative to a vertical centerline axis through the cap fitting 142, so that rotation of the outer cap 76 relative to the inner cap 74 varies the open flow area of the resultant cooperatively formed drip passage. In a preferred form, the flow port 80 in the inner cap 74 comprises a generally rectangular slot (FIG. 10) extending with a radial component of direction, whereas the flow port 82 in the outer cap 78 comprises a crescent-shaped slot (FIG. 11) extending generally circumferentially with respect to a center axis of the cap fitting 142.

Figures 12, 13:
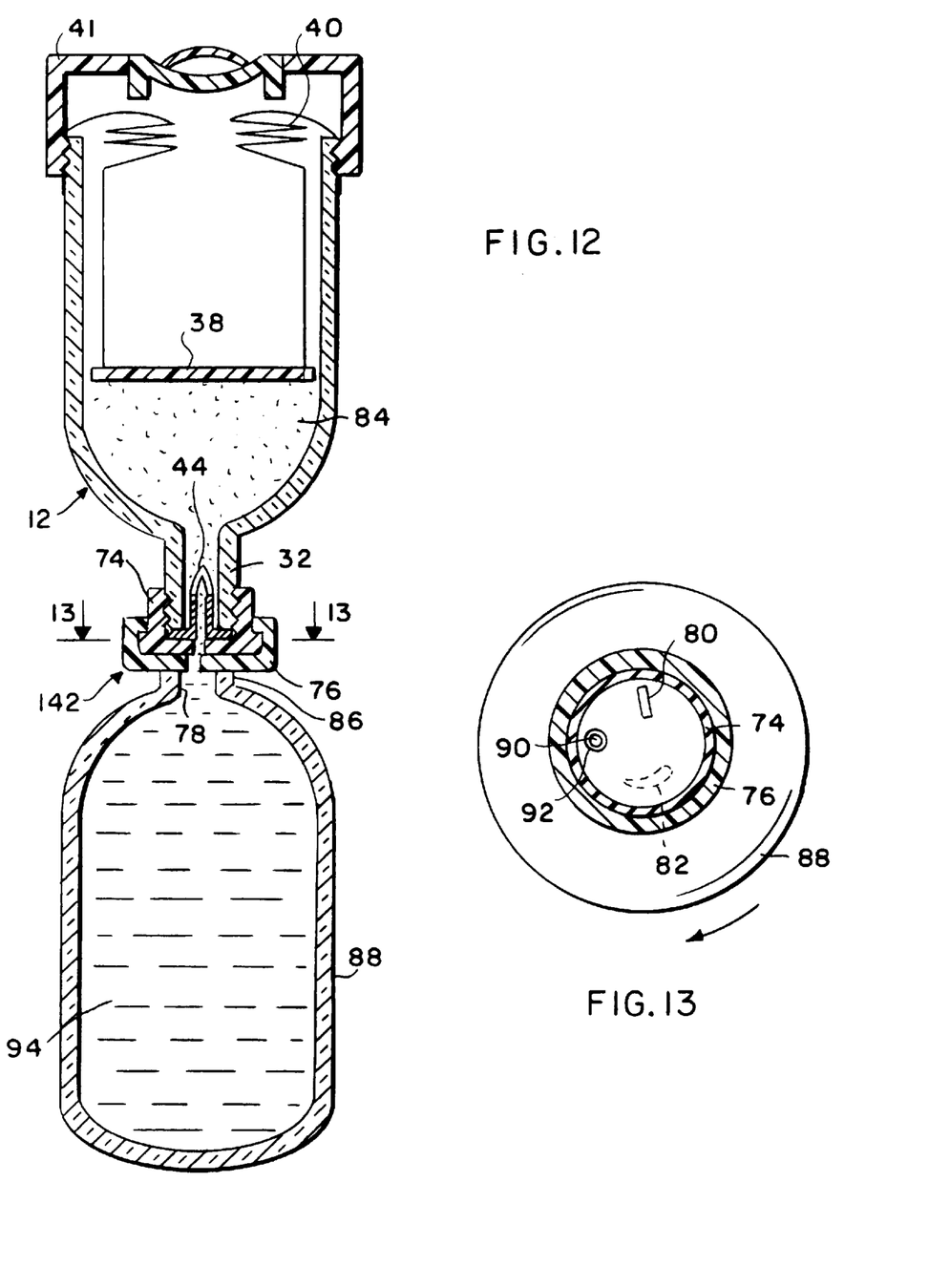
FIG. 12 is a vertical sectional view illustrating the variable volume bottle of FIG. 1 initially assembled with an auxiliary fluid-containing bottle for receiving water or the like used to dissolve a medication in powder form of the like prior to administration of the resultant solution to a patient.
FIG. 13 is a horizontal sectional view taken generally on the line 13—13 of FIG. 12.

The modified cap fitting 142 further comprises a convenient structure for introducing a fluid such as water or saline solution into the variable volume bottle 12 for mixture with and dissolution of a soluble medication contained typically in powder form within the bottle, prior to coupling of the bottle with the infusion tubing 26 for administration of the resultant solution to the patient. FIG. 12 shows the cap fitting 142 mounted on the neck 32 of the variable volume bottle 12 having the soluble medication 84 contained therein. The lower flange 78 on the outer cap 76 is received into the open mouthed neck 86 of a solvent-containing bottle 88. The outer cap 76 is rotatably positioned relative to the inner cap 74 so that the variable flow ports 80, 82 are out of alignment with each other, as viewed in FIG. 13. However, a pair of larger auxiliary flow ports 90 and 92 formed in the inner and outer caps 74,76 are rotatably aligned to permit flow of the solvent fluid 94 from the solvent bottle 88 into the variable volume bottle 12. To achieve this flow, the interconnected bottles 12 and 88 are inverted from the position depicted in FIG. 12, whereupon the solvent fluid drains through the auxiliary ports 90, 92 into the bottle 12 for dissolution of the soluble medication 84 to form the medical fluid 14 to be administered to the patient 16. Such dispensing of the fluid 14 to the patient may occur by uncoupling the cap fitting flange 78 from the bottle 88, and coupling the flange 78 with the infusion tubing 26 as previously shown and described in FIG. 9.

Accordingly, the improved variable volume bottle 12 and related medication dispensing system 10 of the present provides a relatively simple arrangement for delivering a selected medical fluid to a patient by intravenous infusion or the like. The rate of flow of the medical fluid to the patient can be closely monitored and variably set for accurate delivery in accordance with the specific medication and patient requirements.

A variety of further modifications and improvements in and to the variable volume bottle and related dispensing system will be apparent to those persons skilled in the art. Accordingly, no limitation on the invention is intended by way of the foregoing description and accompanying drawings, except as set forth in the appended claims.

What is claimed is:

1. A medical fluid infusion system, comprising:
   a variable volume bottle including a hollow bottle body having an open neck at one end, and an open base end;

a piercable septum mounted over and normally closing said bottle neck;

said bottle further including a base plate slidably received within said base end of said bottle body, said bottle body and said base plate cooperatively defining an interior volume for receiving a selected medical fluid for administration to a patient; and said bottle being adapted for flow of the medical fluid through said neck for administration to a patient when said bottle is supported in an elevated position relative to the patient and inverted with said neck generally at a lower end of said bottle body and with said base end generally at an upper end of said bottle body, said base plate descending within said bottle body to track the level of the medical fluid therein as the medical fluid is dispensed therefrom through said neck.

2. The medical fluid infusion system of claim 1 wherein said open neck and said base end of said bottle body are formed generally at opposite ends of said bottle body.

3. The medical fluid infusion system of claim 1 further including means for sealingly interconnecting said base plate with said bottle body.

4. The medical fluid infusion system of claim 1 further including a generally annular seal membrane interconnecting said base plate with said bottle body generally at said base end thereof.

5. The medical fluid infusion system of claim 1 further including a base cap removably mounted on said base end of said bottle body.

6. The medical fluid infusion system of claim 1 further including support means for supporting said bottle in an inverted orientation and in an elevated position relative to a patient.

7. The medical fluid infusion system of claim 1 further including a length of infusion tubing, and fitting means for coupling said infusion tubing to said neck, said fitting means including spike means for piercing said septum.

8. A medical fluid infusion system, comprising:

a variable volume bottle including a hollow bottle body having an open neck at one end, and an open base end;

said bottle further including a base plate slidably received within said base end of said bottle body, said bottle body and said base plate cooperatively defining an interior volume for receiving a selected medical fluid for administration to a patient;

a length of infusion tubing, fitting means for coupling said infusion tubing in flow communication with said neck, and a flow rate controller for regulating the rate of fluid flow through said infusion tubing to a patient;

said flow rate controller including a pair of interfitting cap members each having a primary flow port and a secondary flow port formed therein for selective alignment to define an inflow passage for introduction of a selected medical fluid into said bottle, said primary flow ports being out of alignment with each other when said secondary flow ports are aligned with each other, and said secondary flow ports being out of alignment with each other when said primary flow ports are aligned with each other, at least one of said cap members being movable relative to the other of said cap members for partially overlapping said primary flow ports to define a variable area outlet port and thereby regulate the fluid flow rate through said infusion tubing to a patient; and said bottle being adapted for flow of the medical fluid through said neck for administration to a patient when said bottle is supported in an elevated position relative to the patient and inverted with said neck generally at a lower end of said bottle body and with said base end generally at an upper end of said bottle body, said base plate descending within said bottle body to track the level of the medical fluid therein as the medical fluid is dispensed therefrom through said neck.

9. The medical fluid infusion system of claim 8 wherein said flow rate controller comprises a resilient nipple having a nipple port formed therein.

10. The medical fluid infusion system of claim 9 wherein said flow rate controller further comprises clamp means for constricting said nipple to set the open flow area defined by said nipple port and thereby regulate the fluid flow rate through said nipple port.

11. The medical fluid infusion system of claim 8 further including a flow sensor unit for monitoring the volume of fluid dispensed from said bottle.

12. The medical fluid infusion system of claim 11 wherein said flow sensor unit further monitors the rate of fluid flow from said bottle.

13. The medical fluid infusion system of claim 12 further including monitor means responsive to said flow sensor unit for adjustably setting said flow rate controller.

14. A medical fluid infusion system, comprising:

a variable volume bottle including a hollow bottle body having an open neck at one end, and an open base end;

said bottle further including a base plate slidably received within said base end of said bottle body, said bottle body and said base plate cooperatively defining an interior volume for receiving a selected medical fluid for administration to a patient;

said bottle being adapted for flow of the medical fluid through said neck for administration to a patient when said bottle is supported in an elevated position relative to the patient and inverted with said neck generally at a lower end of said bottle body and with said base end generally at an upper end of said bottle body, said base plate descending within said bottle body to track the level of the medical fluid therein as the medical fluid is dispensed therefrom through said neck; and a flow sensor unit for monitoring the volume of fluid dispensed from said bottle, wherein said flow sensor unit comprises a sensor housing having a sensor arm movably mounted therein, said sensor arm having one end for engaging and tracking said base plate as said base plate descends within said bottle body upon dispensing of medical fluid therefrom, said sensor arm having a contact thereon for displacement past a succession of contact pads within said sensor housing for generating a succession of electrical signals representative of the volume of fluid dispensed from said bottle.

15. The medical fluid infusion system of claim 14 further including a monitor for receiving said succession of electrical signals, and for indicating the volume of fluid dispensed form said bottle.

16. The medical fluid infusion system of claim 14 wherein said one end of said sensor arm further includes a weighted slug.

17. A medical fluid infusion system, comprising:

a variable volume bottle including a hollow bottle body having an open neck at one end, and an open base end disposed opposite said neck;

said bottle further including a base plate slidably received within said base end of said bottle body, said bottle body and said base plate cooperatively defining an interior volume for receiving a selected medical fluid for administration to a patient;

a length of infusion tubing;

fitting means for coupling said infusion tubing in flow communication with said neck;

said bottle being adapted for flow of the medical fluid through said neck and said infusion tubing for administration to a patient when said bottle is supported in an elevated position relative to the patient and inverted with said neck generally at a lower end of said bottle body and with said base end generally at an upper end of said bottle body, said base plate descending within said bottle body to track the level of the medical fluid therein as the medical fluid is dispensed therefrom through said neck; and a flow sensor unit for monitoring the volume of fluid dispensed from said bottle, said flow sensor unit including means for engaging and tracking said base plate as said base plate descends within said bottle body upon dispensing of the fluid from said bottle.

18. The medical fluid infusion system of claim 17 further including a flow rate controller for regulating the rate of fluid flow though said infusion tubing to a patient.

19. The medical fluid infusion system of claim 18 wherein said flow rate controller comprises a resilient nipple having a nipple port formed therein.

20. The medical fluid infusion system of claim 19 wherein said flow rate controller further comprises clamp means for variably constricting said nipple to variably set the open flow area defined by said nipple port and thereby variably regulate the fluid flow rate through said nipple port.

21. The medical fluid infusion system of claim 18 wherein said flow rate controller comprises a pair of interfitting cap members each having a primary flow port formed therein, at least one of said cap members being movable relative to the other of said cap members for partially overlapping said primary flow ports to define a variable area outlet port and thereby regulate the fluid flow rate through said infusion tubing to a patient.

22. The medical fluid infusion system of claim 18 further including monitor means responsive to said flow sensor unit for adjustably setting said flow rate controller.

23. The medical fluid infusion system of claim 17 further including means for sealingly interconnecting said base plate with said bottle body.

24. The medical fluid infusion system of claim 17 wherein said flow sensor unit comprises a sensor housing, said means for engaging and tracking said base plate comprising a sensor arm movably mounted within said sensor housing and having one end for engaging and tracking said base plate as said base plate descends within said bottle body upon dispensing of medical fluid therefrom, said sensor arm having at least one contact thereon for displacement past a succession of contact pads within said sensor housing for generating a succession of electrical signals representative of the volume of fluid dispensed from said bottle.

25. The medical fluid infusion system of claim 24 further including a monitor for receiving said succession of electrical signals, and for indicating the volume of fluid dispensed from said bottle.

* * * * *